United States Patent [19]

Yonemitsu et al.

[11] 4,059,582

[45] Nov. 22, 1977

[54] PROCESS FOR PREPARING ADENINE

[75] Inventors: Eiichi Yonemitsu, Kashiwa; Tomiya Isshiki, Tokyo; Yasuhiko Kijima, Matsudo, all of Japan

[73] Assignee: Mitsubishi Gas Chemical Company, Inc., Tokyo, Japan

[21] Appl. No.: 598,697

[22] Filed: July 24, 1975

[30] Foreign Application Priority Data

July 31, 1974 Japan .................................. 49-87818
Sept. 24, 1974 Japan ................................ 49-109720

[51] Int. Cl.$^2$ ........................................... C07D 473/34
[52] U.S. Cl. .................................................... 260/252
[58] Field of Search ........................................ 260/252

[56] References Cited

U.S. PATENT DOCUMENTS 2,534,331 12/1950 Woodward .......................... 260/309
3,670,007 6/1972 Ferris .................................... 260/252

FOREIGN PATENT DOCUMENTS 44,10796 5/1969 Japan .................................... 260/252
1,394,322 3/1964 France ................................. 260/252

OTHER PUBLICATIONS

Rappoport, "The Chemistry of the Cyano Group", Interscience (1970), pp. 506-509.
Ferris et al., "JACS," 87, pp. 4976-4977 (1965).
Sanchez et al., "Science," vol. 153, pp. 72 & 73 (1966).
Shaw, J. Biol. Chem., vol. 185, pp. 439-447 (1950).

Primary Examiner—Donald G. Daus
Assistant Examiner—D. B. Springer
Attorney, Agent, or Firm—Brooks, Haidt, Haffner & Delahunty

[57] ABSTRACT

Adenine is prepared by reacting at least one member selected from the class of diaminomaleonitrile and diaminofumaronitrile, a formic acid derivative and at least one member selected from the class of ammonia and ammonium salts in the presence or absence of a solvent.

13 Claims, No Drawings

PROCESS FOR PREPARING ADENINE

BACKGROUND OF THE INVENTION

1. Field of the Invention

This invention relates to a novel process for preparing adenine starting from diaminomaleonitrile (hereinafter called "DAMN") and/or diaminofumaronitrile (hereinafter called "DAFN").

2. Description of the Prior Art

Adenine is widely present in tissues of animals and plants as a main constituent of nucleic acids and coenzymes and plays an important role. Adenine and its derivatives are known as having pharmacological effects and are very useful in medical and biochemical fields. Furthermore, adenine is an important intermediate for preparing 5'-nucleotides, used as seasoning.

There have been, heretofore, proposed several dozens of methods including the methods used only in the laboratory, for preparing adenine. As commercial one step methods, there are, for example, a method comprising reacting hydrogen cyanide or other cyanide with ammonia or an ammonium salt substantially in the absence of moisture (Japanese Patent Publication No. 10113/1966) and a method comprising reacting formamide with an acid anhydride derived from phosphorus or sulfur, or acid halide (Japanese Patent Publication No. 6955/1968). However, in the former there is used hydrogen cyanide, a very poisonous compound, under high pressure and a lot of by-products are formed, as are, insoluble colored matter produced by polymerization of hydrogen cyanide. In view of the foregoing, the former is not satisfactory as a commercial process.

In the latter, an acid anhydride or acid halide should be used so that highly corrosion-resistant materials are necessary and consequently the commercial plant is very expensive. In addition, a lot of by-products, acidic products derived from phosphorous or sulfur compounds, should be treated and the reaction should be carried out under pressure. Therefore, neither is the latter satisfactory as a commercial process. For improving the above methods, there have been proposed methods comprising reacting an amidine salt with DAMN or DAFN, for example, those disclosed in Japanese Patent Publication Nos. 4374/1971 and 20623/1972. DAMN can be easily and safely produced from hydrogen cyanide and DAFN can be easily derived from DAMN.

In the above mentioned methods, the reaction procedure is easy and safe and complicated by-products are not produced so that adenine can be easily isolated. However, in these methods an amidine salt is used as one of the starting materials. The amidine salt is a special organic chemical material which is not commercially available. Even if it were commercially available, it would be very expensive. Further it is described that the presence of even a small amount of ammonia in the reaction system decreases the yield of adenine. In view of the foregoing these methods are not commercially satisfactory.

SUMMARY OF THE INVENTION

According to the present invention, there is provided a process for preparing adenine comprising reacting at least one member selected from the class of diaminomaleonitrile and diaminofumaronitrile, a formic acid derivative and at least one member selected from the class of ammonia and ammonium salts in the presence or absence of a solvent.

It is an object of the invention to provide a novel process for preparing adenine free from complicated by-products.

It is another object of the invention to provide a novel process for preparing adenine in which the end product, adenine, can be easily recovered from the reaction mixture.

It is a further object of the invention to provide a novel process for preparing adenine from commercially available and inexpensive starting materials.

It is still another object of the invention to provide a novel process for preparing adenine starting from non-poisonous materials.

The present invention is based on the novel reaction which was discovered by the present inventors.

DESCRIPTION OF THE PREFERRED EMBODIMENTS

In the present invention, DAMN and DAFN as starting materials may be used alone or in admixture and when used in admixture, the ratio of DAMN to DAFN may be optionally selected.

As formic acid derivatives used in the present invention, there may be mentioned preferably formic acid salts such as ammonium formate and the like, formic acid amides such as formamide and the like, orthoformic acid esters such as methyl orthoformate, ethyl orthoformate and the like, and formic acid esters such as methyl formate, ethyl formate and the like.

The amount of the formic acid derivative is not critical, but is usually not less than 100g., preferably 500 – 10,000g. per one mole of DAMN or DAFN, from an economic point of view. When the amount of formic acid derivative is less than 100g., the yield of adenine tends to decrease.

The ammonium salt used in the present invention may be defined as all ammonium salts derived from an organic or inorganic acid and ammonia.

The acid constituting the ammonium salt may be an organic acid such as formic acid, acetic acid, citric acid, tartaric acid or the like, and an inorganic acid such as phosphoric acid, hydrochloric acid, sulfuric acid, nitric acid and the like. The amount of ammonia and/or ammonium salt used in the present invention may be not less than the catalytic amount.

It is preferable that the amount of ammonia and/or ammonium salt be not less than 4% by weight based on the reaction mixture. In the absence of lower alcohols in the reaction mixture, it is particularly preferably not less than 5%.

Ammonium formate is both a formic acid derivative and an ammonium salt, so that in the present invention, for convenience, half of the amount of ammonium formate is regarded as the amount of formic acid derivative, and the other half of the amount of ammonium formate is regarded as the amount of ammonium salt.

The reaction temperature is not particularly critical, but the reaction is carried out smoothly at 80° – 200° C, preferably 100° – 180° C. At a reaction temperature lower than 80° C the reaction rate is lower while at a reaction temperature higher than 200° C the starting materials are susceptible to decomposition.

The reaction may carried out for from several minutes to 24 hours or longer, depending upon the reaction temperature. At temperatures lower than 80° C, it takes 24 – 48 hours to complete the reaction. At temperatures higher than 200° C, the reaction is substantially completed immediately after mixing the starting materials, but undesirable side-reactions also occur. At a reaction temperature between 100° and 180° C the raction is usually completed in 1 - 10 hours.

The reaction of the present invention can sufficiently proceed usually at atmospheric pressure.

In order to prevent low boiling point materials such as ammonia, lower alcohols and the like from escaping, according to the reaction conditions, it is preferable to effect the reaction in a sealed vessel.

A solvent such as lower alcohols, benzene, acetamide, dimethylformamide and the like may be used as a diluent so far as the solvent does not suppress the reaction.

Among the solvents, lower alcohols having 1 - 4 carbon atoms such as methanol, ethanol, propanol, and butanol can serve to facilitate the main reaction of the present invention resulting in high yield.

When the lower alcohols are used in the reaction mixture, the amount of the lower alcohols is usually 1 - 20% by weight, preferably 2 - 15% by weight, based on the reaction mixture. When the amount of lower alcohols is less than 1% by weight, the effect of the lower alcohol added is not noticeable, but when it is more than 20% by weight, the main reaction is rather suppressed.

The process of the present invention may be carried out in any systems; batch systems, semi-batch systems and continuous systems.

According to the process of the present invention, the reaction products do not contain complicated by-products and thereby recovery of adenine is far easier than the conventional processes, and the starting materials are commercially available and inexpensive so that the process of the present invention is a commercially advantageous process.

The following examples illustrate the process of the present invention. In the following examples, the yield of adenine is the yield based on DAMN or DAFN assuming that one mole of adenine is produced from one mole of DAMN and/or DAFN. The yield is calculated from amount of adenine present in the reaction mixture quantitatively determined by chromatography unless otherwise specified.

EXAMPLE 1

135 g. of formamide, 3.01 g. of DAMN (purity of 97.3%. In the following examples there was used DAMN of the same purity as this), and 30 g. of ammonium formate were mixed and the admixture was heated at 150° C for 5 hours. The resulting reaction mixture contained 1.69 g. of adenine. The yield is 46.1%.

EXAMPLE 2

50 g. of formamide containing 10% ammonia and 1.00 g. of DAMN were mixed and heated in a sealed tube at 150° C for 5 hours. Adenine was produced in a 43.5% yield.

EXAMPLE 3

135 g. of acetamide, 3.02 g. of DAMN and 30 g. of ammonium formate were mixed and heated at 150° C for 5 hours. Adenine was obtained in a 17.7% yield. The resulting reaction mixture was concentrated under reduced pressure to obtain a dark green residue. The residue was extracted with a 3 N aqueous ammonia. The extracts were concentrated under reduced pressure and acidified with hydrochloric acid. The resulting solution was adsorbed on activated carbon packed in a column, washed with water and eluted with a developing solution (water : methanol : 28% aqueous ammonia (volume ratio) = 6 : 6 : 1). The effluents were collected and concentrated under reduced pressure and the resulting residues were recrystallized to obtain 520 mg. of white crystals. The infrared absorption spectrum of the crystals coincided with that of an authentic sample. The results of elementary analysis of the product agree with the calculated values of adenine ($C_5H_5N_5$) very well as shown below.

|  | C (%) | H (%) | N (%) |
| --- | --- | --- | --- |
| Calculated: | 44.44 | 3.73 | 51.83 |
| Found: | 44.0 | 3.7 | 52.3 |

EXAMPLE 4

Repeating the procedure of Example 1 except that other ammonium salts were used in place of ammonium formate, the following results were obtained:

| Ammonium salt | Yield of Adenine |
| --- | --- |
| Ammonium acetate | 40.4 % |
| Triammonium citrate | 43.7 |
| Diammonium hydrogen citrate | 27.5 |
| Diammonium hydrogen phosphate | 24.6 |
| Ammonium tartarate | 28.9 |
| Ammonium chloride | 15.6 |
| Ammonium sulfate | 16.4 |
| Ammonium nitrate | 15.8 |

EXAMPLE 5

50 g. of formamide containing 10% ammonia, 1.00 g. of DAMN and 5 g. of ammonium formate were mixed and heated in a sealed tube at 150° C for 5 hours. Adenine was produced in a 48.4% yield.

EXAMPLE 6

270 g. of formamide and 60 g. of ammonium formate were mixed and kept at 150° C to avoid humidity. To the resulting mixture was continuously added 30.6 g. of DAMN over 8 hours and the mixture was then kept for a further 3 hours at 150° C. Adenine was obtained in a 46.2% yield. The resulting reaction mixture was concentrated under reduced pressure to recover the remaining formamide. The residue was extracted with a 3 N aqueous ammonia. The extracts were concentrated under reduced pressure, acidified with hydrochloric acid, treated with activated carbon, and the resulting solution was adjusted to pH 7.0 to precipitate crystals, followed by recrystallization with water to obtain 14.8 g. of white crystals. The infrared absorption spectrum of these crystals was the same as that of an authentic sample. The results of elementary analysis of the crystal agreed with the calculated values of adenine ($C_5H_5N_5$) very well.

|  | C (%) | H (%) | N (%) |
| --- | --- | --- | --- |
| Calculated: | 44.44 | 3.73 | 51.83 |
| Found: | 44.5 | 3.7 | 51.7 |

EXAMPLE 7

45 g. of ammonium formate and 675 mg. of DAMN were kept at 150° C for 5 hours. Adenine was produced in a 14.6% yield.

EXAMPLE 8

30 g. of methyl formate, 667 mg. of DAMN and 30 g. of ammonia were mixed and kept at 150° C for 5 hours in a sealed tube. Adenine was produced in a 30.9% yield.

EXAMPLE 9

The procedure of Example 8 was repeated except that 30 g. of ethyl formate was used in place of methyl formate. Adenine was obtained in a 29.5% yield.

EXAMPLE 10

The procedure of Example 8 was repeated except that 30 g. of methyl orthoformate was used in place of methyl formate, and adenine was obtained in a 13.1% yield.

EXAMPLE 11

The procedure of Example 8 was repeated except that 30 g. of ethyl orthoformate was used in place of methyl formate. Adenine was obtained in an 11.4% yield.

EXAMPLE 12

The procedure of Example 1 was repeated except that the reaction was carried out at 170° C for 2 hours or at 100° C for 10 hours in place of at 150° C for 5 hours. Adenine was obtained in 43.4% and 30.0% yields, respectively.

EXAMPLE 13

45 g. of formamide, 1.00 g. of DAFN and 10 g. of ammonium formate were mixed and kept at 150° C for 5 hours and adenine was obtained in a 48.1% yield.

EXAMPLE 14

The procedure of Example 13 was repeated except that a mixture of 0.50 g. of DAMN and 0.50 g. of DAFN in place of DAFN alone to produce adenine in a 48.5% yield.

EXAMPLE 15

50 g. of formamide containing 10% ammonia and 6.94 g. of DAMN were mixed and heated at 150° C for 5 hours in a sealed tube to give adenine in a 9.8% yield.

EXAMPLE 16

47.5 g. of formamide containing 5% ammonia and 1.00 g. of DAMN were mixed and heated at 150° C for 5 hours in a sealed tube to give adenine in a 32.1% yield.

EXAMPLE 17

47.5 g. of formamide containing 5% ammonia, 1.00 g. of DAMN and 3 g. of methanol were mixed and heated at 150° C for 5 hours in a sealed tube to produce adenine in a 42.0% yield.

EXAMPLE 18

45 g. of formamide, 0.67 g. of DAMN, 27 g. of ammonium formate and 3 g. of methanol were mixed and heated at 150° C for 5 hours in a sealed tube to give adenine in a 58.4% yield.

EXAMPLE 19

45 g. of formamide, 1.00 g. of DAMN, 10 g. of ammonium formate and 3 g. of ethanol were mixed and heated at 150° C for 5 hours in a sealed tube to give adenine in a 55.4% yield.

EXAMPLE 20

Repeating the procedure of Example 19 except that isopropyl alcohol was used in place of ethanol, there was obtained adenine in a 54.4% yield.

EXAMPLE 21

Repeating the procedure of Example 19 except that 3 g. of other lower alcohols was used in place of ethanol, adenine was obtained in the following yields:

| Alcohol | Yield of Adenine(%) |
| --- | --- |
| 1 - propanol | 54.0 |
| 1 - butanol | 50.5 |
| 2 - butanol | 52.3 |
| isobutyl alcohol | 50.0 |
| tert-butyl alcohol | 51.0 |

EXAMPLE 22

45 g. of formamide, 1.00 g. of DAMN, 10 g. of ammonium formate, and 9.0 g. of isopropyl alcohol were mixed and kept at 170° C for 2 hours in a sealed tube to give adenine in a 54.2% yield.

EXAMPLE 23

Repeating the procedure of Example 19 except that the following ammonium salts were used in place of ammonium formate, adenine was obtained in the yields as shown below:

| Ammonium salt | Yield of Adenine(%) |
| --- | --- |
| ammonium acetate | 53.5 |
| triammonium citrate | 54.6 |
| ammonium nitrate | 22.0 |

EXAMPLE 24

50 g. of formamide containing 10% ammonia, 1.00 g. of DAMN, 10 g. of ammonium formate, and 3 g. of methanol were mixed and heated at 150° C for 5 hours in a sealed tube to give adenine in a 59.2% yield.

EXAMPLE 25

45 g. of formamide, 1.00 g. of DAFN, 10 g. of ammonium formate and 3 g. of methanol were mixed and kept in a sealed tube at 150° C for 5 hours to give adenine in a 55.9% yield.

We claim:

1. A process for preparing adenine directly which comprises reacting at least one member selected from the group consisting of diaminomaleonitrile and diaminofumaronitrile, a formic acid derivative selected from the group consisting of ammonium formate, formamide, orthoformic acid methyl and ethyl esters, and formic acid methyl and ethyl esters, and at least one member selected from the group of ammonia and ammonium salts in the presence or absence of a solvent, the amount of formic acid derivative being not less than 100 g per mole of nitrile.

2. A process according to claim 1 in which the solvent is a lower alcohol having 1 - 4 carbon atoms.

3. A process according to claim 2 in which the lower alcohol is selected from the group consisting of methanol, ethanol, 1-propanol, isopropyl alcohol, 1-butanol, 2-butanol, isobutyl alcohol, and tert-butyl alcohol.

4. A process according to claim 1 in which the solvent is selected from the group consisting of benzene, acetamide and dimethyl formamide.

5. A process according to claim 1 in which the formic acid derivative is selected from the group consisting of formic acid salts, formic acid amides, orthoformic acid esters and formic acid esters.

6. A process according to claim 1 in which the amount of the formic acid derivative is 500 – 10,000 g. per mole of the nitrile.

7. A process according to claim 1 in which the acid constituting the ammonium salt in an organic or inorganic acid.

8. A process according to claim 7 in which the acid constituting the ammonium salt is selected from the group consisting of formic acid, acetic acid, citric acid, tartaric acid, phosphoric acid, hydrochloric acid, sulfuric acid and nitric acid.

9. A process according to claim 1 in which the reaction is carried out at 80° – 200° C.

10. A process according to claim 9 in which the reaction is carried out at 100° – 180° C.

11. A process according to claim 1 in which the amount of the lower alcohol is 1 – 20% by weight based on the reaction mixture.

12. A process according to claim 1 in which the amount of the lower alcohol is 2 – 15% by weight based on the reaction mixture.

13. A process according to claim 1 in which the amount of the ammonia or ammonium salt is not less than 4% by weight based on the reaction mixture.

* * * * *

UNITED STATES PATENT AND TRADEMARK OFFICE
CERTIFICATE OF CORRECTION

PATENT NO. : 4,059,582
DATED : November 22, 1977
INVENTOR(S) : EIICHI YONEMITSU ET AL It is certified that error appears in the above-identified patent and that said Letters Patent are hereby corrected as shown below:

Column 7, line 14, change "in" to --is--.

Signed and Sealed this

Fourth Day of April 1978

[SEAL]

Attest:

RUTH C. MASON
Attesting Officer

LUTRELLE F. PARKER
Acting Commissioner of Patents and Trademarks